US009422470B2

(12) United States Patent
Xu et al.

(10) Patent No.: US 9,422,470 B2
(45) Date of Patent: Aug. 23, 2016

(54) METHOD FOR SELECTION OF SURFACTANTS IN WELL STIMULATION

(75) Inventors: Liang Xu, Houston, TX (US); Qiang Fu, Houston, TX (US)

(73) Assignee: Multi-Chem Group, LLC, San Angelo, TX (US)

(*) Notice: Subject to any disclaimer, the term of this patent is extended or adjusted under 35 U.S.C. 154(b) by 902 days.

(21) Appl. No.: 13/611,523

(22) Filed: Sep. 12, 2012

(65) Prior Publication Data

US 2013/0067999 A1    Mar. 21, 2013

Related U.S. Application Data

(60) Provisional application No. 61/573,967, filed on Sep. 15, 2011.

(51) Int. Cl.
*G01N 37/00*    (2006.01)
*C09K 8/60*    (2006.01)
*G01N 13/02*    (2006.01)
*C09K 8/68*    (2006.01)
*C09K 8/584*    (2006.01)
*C09K 8/86*    (2006.01)

(52) U.S. Cl.
CPC ............. *C09K 8/602* (2013.01); *C09K 8/584* (2013.01); *C09K 8/68* (2013.01); *C09K 8/86* (2013.01); *G01N 13/02* (2013.01); *G01N 2013/0275* (2013.01)

(58) Field of Classification Search
CPC ........................... G01N 33/6893; G01N 33/49
USPC ........................................................ 73/61.43
See application file for complete search history.

(56) References Cited

U.S. PATENT DOCUMENTS

| 4,722,396 A | 2/1988 | Balzer |
| 4,836,283 A | 6/1989 | Loza et al. |
| 2002/0023752 A1 | 2/2002 | Qu et al. |
| 2012/0152548 A1 | 6/2012 | Hinkel et al. |

FOREIGN PATENT DOCUMENTS

| WO | 2011005746 A1 | 1/2011 |
| WO | 2011073608 A1 | 6/2011 |

OTHER PUBLICATIONS

David B. Levitt et al., "Identification and Evaluation of High-Performance EOR Surfactants." SPE Reservoir Evaluation and Engineering [online], Apr. 2009 [Retreived on May 2, 2013], vol. 12, Iss. 2, pp. 243-253, Retrieved from the Internet: <URL: http://www.onepetro.org/mslib/servlet/onepetropreview?id=SPE-100089-PA>, p. 243 (Summary and Introduction).
Extended European Search Report in related European application No. 12831838.3, mailed Nov. 12, 2015 (9 pages).
(Continued)

*Primary Examiner* — Hezron E Williams
*Assistant Examiner* — Rodney T Frank
(74) *Attorney, Agent, or Firm* — Craig W. Roddy; Baker Botts L.L.P.

(57) ABSTRACT

A method of determining the suitability of a surfactant for use in a formation can include sampling water in the formation, providing at least two surfactants, and mixing each of the surfactants with the formation water to form surfactant/water samples. The method can further include determining the solubility of each surfactant with the formation water, comparing the solubility of each surfactant with the other surfactant, and assigning a solubility performance value for each surfactant based on its solubility in the formation water sample compared to the other surfactant.

12 Claims, 5 Drawing Sheets

(56) References Cited

OTHER PUBLICATIONS

Lee et al.: "The Effectiveness of Surfactants for Remediation of Organic Pollutants in the Unsaturated Zone", Journal of Soil Contamination, vol. 8, No. 1, Jan. 1, 1999, pp. 39-62, XP055191722, ISSN: 1058-8337, DOI: 10.1080/10588339991339225, p. 41-57.

Aoudia et al.: "Novel Surfactants for Ultralow Interfacial Tension in a Wide Range of Surfactant Concentration and Temperature", Journal of Surfactants and Detergents, Springer, Berlin, DE, vol. 9 No. 3, Jul. 1, 2006 pp. 287-293, XP001245898, ISSN: 1097-3958, DOI: 10.1007/s11743-006-5009-9 p. 288-292.

Abdul et al.: "Selection of Surfactants for the Removal of Petroleum Products from Shallow Sandy Aquifers", Ground Water, vol. 28, No. 6, Jan. 1, 1990, pp. 920-926, XP055191471, p. 920-925.

METHOD FOR SELECTION OF SURFACTANTS IN WELL STIMULATION

BACKGROUND

1. Field

The disclosure relates generally to the field of fracturing fluids used in fracturing subterranean formations during hydrocarbon recovery. More specifically the disclosure relates to methods for selecting surfactants used in fracturing fluids.

2. Background Art

Hydraulic fracturing is a formation stimulation technique used to create additional permeability in a producing formation to increase the flow of hydrocarbons toward the wellbore. Typically, during a hydraulic fracturing operation, a high hydraulic pressure is used to fracture the subterranean formation, creating cracks that facilitate the increased flow of hydrocarbons. Often, proppants are used to keep cracks open that are created during the fracturing operation.

Fracturing fluids include a number of components and are most often water-based. These components typically include acids, biocides, breakers, corrosion inhibitors, friction reducers, gels, iron control chemicals, oxygen scavengers, surfactants and scale inhibitors.

Conventional selection for selecting a surfactant typically focuses on one or two attributes of the surfactant. In particular for unconventional oil and gas plays, efficacy of the surfactant chosen for hydraulic fracturing depends on a number of factors, including formation characteristics, oil types, reservoir temperature, and the other elements of the fracturing fluid.

What is needed is a method of determining the efficacy of a surfactant for a fracturing fluid for a particular use.

BRIEF DESCRIPTION OF THE DRAWINGS

The present disclosure is best understood from the following detailed description when read with the accompanying FIGS. It is emphasized that, in accordance with the stand practice in the industry, various features are not drawn to scale. In fact, the dimensions of the various features may be arbitrarily reduced for clarity of discussion.

SUMMARY

Figure 1:
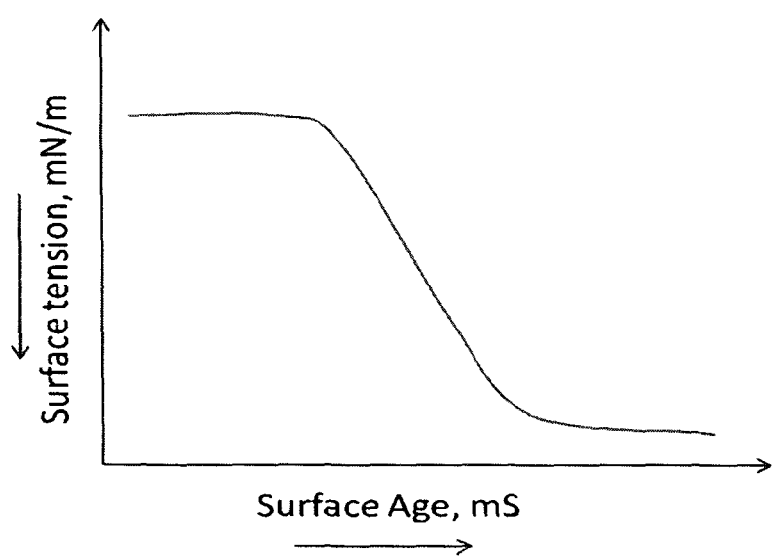
FIG. 1 is an example of a model of dynamic surface tension measurements as a function of time. according to one or more aspects of the present disclosure.

The methods described herein relate generally to the field of gas and oil production. In particular, methods of selecting surfactants for fracturing fluids are described.

In one embodiment of the present disclosure.

DETAILED DESCRIPTION

The disclosure below is not limited to the embodiments, versions or examples described, which are included to enable a person having ordinary skill in the art to make and use the disclosed subject matter when the information in this patent is combined with available information and technology.

Various terms as used herein are shown below. To the extent a term used in a claim is not defined below, it should be given the broadest definition skilled persons in the pertinent art have given that term as reflected in printed publications and issued patents at the time of filing. Further, unless otherwise specified, all compounds described herein may be substituted or unsubstituted and the listing of compounds includes derivatives thereof.

Further, various ranges and/or numerical limitations may be expressly stated below. It should be recognized that unless stated otherwise, it is intended that endpoints are to be interchangeable. Further, any ranges include iterative ranges of like magnitude falling within the expressly stated ranges or limitations. For example, if the detailed description recites a range of from 1 to 5, that range includes all iterative ranges within that range including, for instance, 1.3-2.7 or 4.9-4.95.

The present disclosure describes a number of tests that may be performed to select a particular surfactant for a fracturing fluid. In one embodiment, all of the tests are used. In other embodiments, select tests may be performed. These tests may be performed in any order and the order described below is non-limiting.

The tests include:

1. Water solubility—A surfactant may be tested to if that surfactant is soluble in water. A water solubility test may assist in selecting a surfactant to determine if that surfactant is able to travel with the leading edge of a water front and reach the interior of the rock formation;

2. Emulsion tendency—A visual inspected of oil and water containing surfactants may be performed and emulsion droplet size and zeta potential may be determined to understand the tendency of a surfactant to create aweak or transient oil in water emulsion;

3. Interfacial surface tension measurements between hydrocarbon and surfactant solutions.

4. Wettability-spontaneous imbibitions of surfactants into the rock formation

5. Oil recovery—In the oil recovery test, crushed formation cores or drill cuttings may be saturated with crude oil from the same formation and the surfactant solution is passed through the cores that are packed in a glass column. Effluents are collected and oil recovery by individual surfactants may be quantified.

6. Adsorption to proppants—during fracturing operations, some surfactant molecules can be adsorbed onto the proppant surface and never reach the interior of the reservoir. This test is to quantify how much surfactant molecules are lost to proppants.

Each of the tests above will now be specified in greater detail.

1. Water Solubility

Surfactants that are soluble or dispersible in water may more easily reach the interior of the formation. Because of the surface tension gradient or the Gibbs-Marangoni effect, where surfactants diffuse from the areas of low surface tensions to those of high surface tensions, surfactants can remain at the tip of the water front and further penetrate the formation. In this test, fresh or source water from the formation is typically used and different concentrations of the chosen surfactant is added to the water. If the surfactant is soluble or dispersible, the water typically remains clear or slightly cloudy. If insoluble, the water typically turns turbid or opaque. In certain cases where the surfactant is insoluble, precipitates may be found. In addition to the traditional hydrophile-lipophile balance numbers (HLB) that may be used for water free of high concentrations of divalent ions (hard water) and salts (brine), where surfactants having a HLB less than 4 remain insoluble, a turbidity meter may be used to monitor the cloudiness or turbidity of the solutions.

2. Emulsion Tendency

Shale plays often have low porosity and ultra-low permeability. In some situations, the permeability may be in the nanodarcies or millidarcies ranges. Consequently, the flow path for oil molecules to migrate from the interior of the reservoirs to the artificial propped fractures created in a hydraulic fracturing process may be confined and/or limited. In certain embodiments, a surfactant may be needed to minimize the formation damage induced by large quantities of water and enhance the oil and gas production. Traditionally, a non-emulsifying surfactant is used so that less oil/water emulsion is generated. However, in one embodiment of the present disclosure, a weak emulsifying surfactant may be used to enhance the formation production.

In one embodiment of the present disclosure, an emulsification test is used to quantify the phase separation rates and emulsion droplet size distribution by monitoring the emulsion with dynamic light scattering measurements. Surfactants may then be screened to remove surfactants that may separate too quickly, have a droplet size larger than 10 microns and a loose distribution, resulting in possible poor field production.

3. Interfacial Surface Tension

Dynamic and static surface tension are two physical properties of the surfactants that typically determine the surface tension between air/gas and surfactant solutions. Whether it is at air/liquid or solid/liquid interface, surfactants travel to the interface from the bulk of the solution. The speed with which the surfactants travel plays a significant role in processes where new interfaces are generated.

Dynamic surface tension measurements may record surface tension reduction as a function of time. Dynamic surface tension may relate to processes such as foaming, bubble dynamics, solubilization and detergency, emulsion droplet size and thin film stability. Without being bound by theory, it is believed that as time elapses, there is sufficient time available for more surfactant molecules to travel to and accumulate at the interface. Those molecules may pack tightly at the interface and hence lower the surface tensions between two immiscible phases. A typical measurement is illustrated in FIG. 1 by using a bubble pressure tensiometer such as Kruss BP100. An additional measurement related to this effect may be whether the movement of surfactants to the interface is dominated by diffusion. A characteristic time may be determined and correlated back to the diffusion coefficient of the surfactant.

Lowering interfacial surface tensions (IFT) between surfactant solutions and crude oil or condensate allows mobilization of the oil globules inside the pore space. IFT is typically directly proportional to emulsion droplet size, i.e. the lower IFT, the lower the emulsion droplet size. The oil emulsion droplets typically must be preferably less than 10 microns that they can escape from the tiny pore space in the shale formation. IFT is measured by using a ring or plate method with Kruss K100. To qualify a surfactant, it must lower IFT to preferably lower than 20 mN/m 4. Wettability/Capillary Pressure During a hydraulic fracturing operation, millions of gallons of water may be pumped into the shale formation. Because of the ultralow permeability and nanometer-sized pores in the shale, water tends to display high capillary pressure and imbibe into the pores. If the formation pressure is lower than the capillary pressure of invaded water, the water can get stuck, plug the pores and the oil or gas cannot flow out when the well is put on production. In the presence of surfactants, the high capillary pressure of invaded water may be reduced and the water can be readily returned together with oil and gas, thereby reducing formation damage/plugging and enhancing production.

5. Oil Recovery

Shale core plugs obtained from thousands of feet below the ground are typically of ultralow permeability and contain oil globules that are deeply trapped inside the pore space in the formation. It may not be feasible to pump the surfactant solution directly through a shale core plug because large differential pressure is required. In addition, the oil recovered from shale core plugs is typically so little that the results are not reproducible. With the oil recovery test of the present disclosure, it is possible to differentiate the oil extraction capabilities by various surfactants and surfactant blends.

Adsorption to Proppants

Proppants including sand or ceramic are usually pumped together with surfactants. Some surfactants tend to adsorb onto the proppant surface and hence do not reach the interior of formation. The adsorbed surfactants may be considered to be lost and might not contribute to oil and gas production. The adsorption of surfactants onto the proppants can be evaluated to account for the loss. The loss to proppants can serve as a reference for comparing various surfactants.

EXAMPLES

Example 1

Water Solubility 99.9 gram of source water was poured into a glass bottle. 0.1 grams of a linear ethoxyated alcohol surfactant was added to the source water. The bottle was shaken by hand by hand for 30 seconds and the solution was allowed to stand overnight. A turbidity meter was used to measure the turbidity of the solution. If the value is higher than 20%, preferably 40%, then the surfactant is verified to be soluble or dispersible.

Example 2

Dynamic Surface Tension 100 grams of 1000 parts per million (ppm) of the surfactant in source water was prepared to form a surfactant solution. 70 grams of surfactant solution was added to the measuring container in a bubble pressure tensiometer (e.g. Kruss BP100)

Start the measurement and record the surface tension as a function of surface age time The characteristic time $\tau_d$ and the equilibrium surface tension $\gamma_{eq}$ were determined from the data fitting of the curves, following the equation below:

$$\Delta\gamma(t \gg \tau_d) \cong \Delta\gamma_{eq}\left(1 - \sqrt{\frac{\tau_d}{t}}\right)$$

The diffusion coefficient was determined from the molecular size a and the volume fraction $\phi_b$ of the surfactant:

$$D \cong \frac{1}{\phi_b^2} \frac{a^2}{\pi \tau_d}$$

Figure 2:
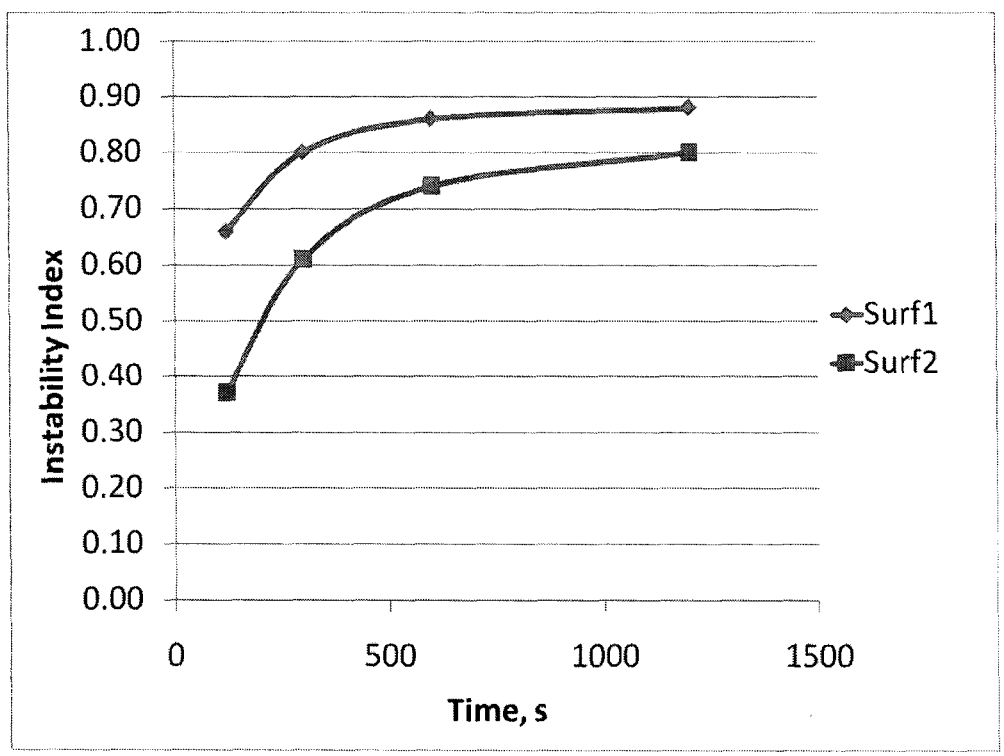
FIG. 2 is a graph of diffusion coefficients of various surfactants in accordance with Example 2.

The diffusion coefficients of various surfactants were compared under different field conditions and the faster surfactants are selected as shown in FIG. 2.

Example 3

Emulsion Tendency

Equal volumes of 1000 ppm surfactant solution and crude oil were combined in a quartz tube (note that condensate may also be used). The tube was shaken with a mechanical shaker. A high speed blender may also be used. The tube was immediately placed in a dynamic scattering device such as Lumi-Sizer or Turbiscan. The data was collected for two hours. The phase separation rates or instability index of emulsions were then calculated from the slopes of the curves by ΔTransmission or BackScattering=$f$(Time).

Figure 3:
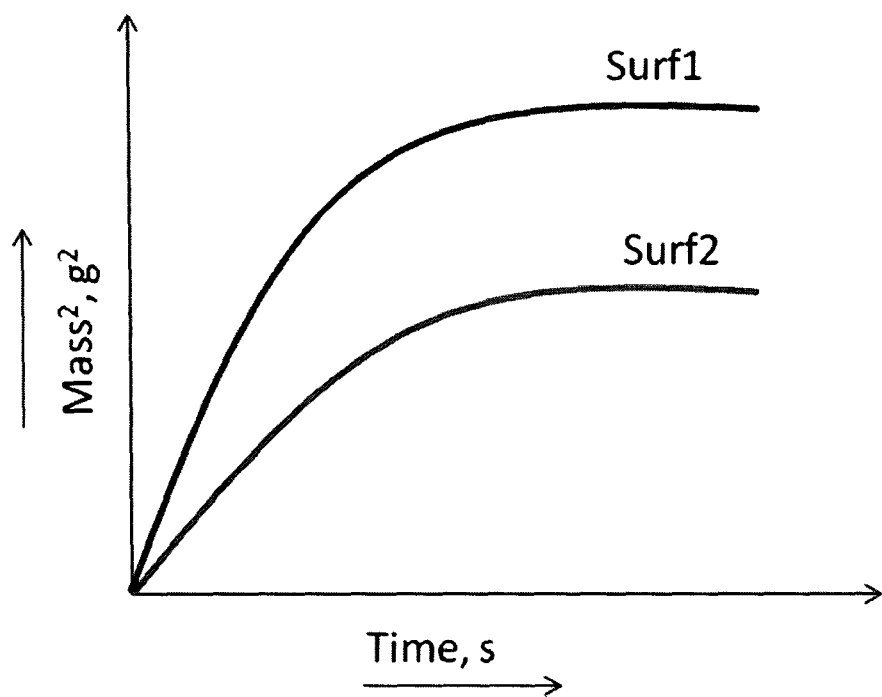
FIG. 3 is a graph comparing the phase separation rates of a non-emulsifying surfactant with a weakly emulsifying surfactant in accordance with Example 3.
Figure 4:
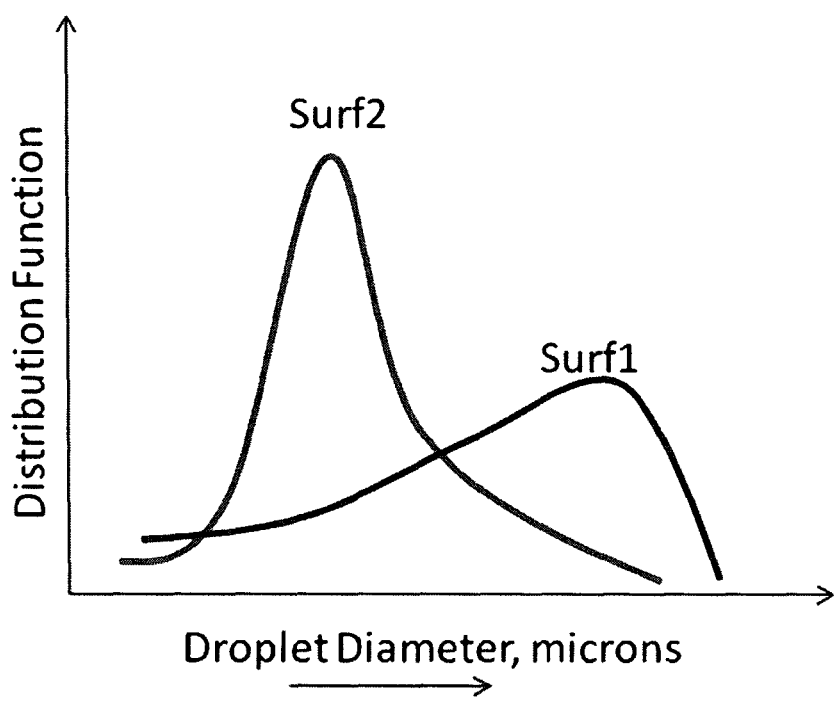
FIG. 4 illustrates the droplet size distributions of a non-emulsifying surfactant with a weakly emulsifying surfactant in accordance with Example 3.

Those values are chosen as a reference to compare the efficiency of surfactants. FIG. 3 compares the phase separation rates of a non-emulsifying surfactant (surf 1-$a$ linear ethoxylated alcohol) and a weakly emulsifying one (surf 2-$a$ linear ethoxylated sulfate). FIG. 4 illustrates the droplet size distributions between surf 1 and surf2.

Example 4

Oil Recovery

Shale core plugs from different depths of the wells were crushed to 80~100 mesh or 149~177 microns to expose the large surfaces in the shale. The crushed core was then saturated with the crude oil from the production well at the formation temperature for an extended period of time. The saturated core was then filtered and dried in a thermal oven The saturated core was packed into a glass column and a surfactant solution of 1000 ppm is pumped through the column a few times at a fixed flow rate. The effluent was collected at the exit of the column and the oil recovery was calculated for each pass, by using infrared spectroscopy. As shown in Table 2, surf 2 has superior oil extraction capability than surf1.

TABLE 2

| Oil Recovery, % | First Pass | Second Pass | Third Pass | Fourth Pass | Residual Oil |
|---|---|---|---|---|---|
| Surf1 | 5 | 5 | 3 | 4 | 83 |
| Surf2 | 10 | 20 | 8 | 12 | 50 |

Example 5

Figure 5:
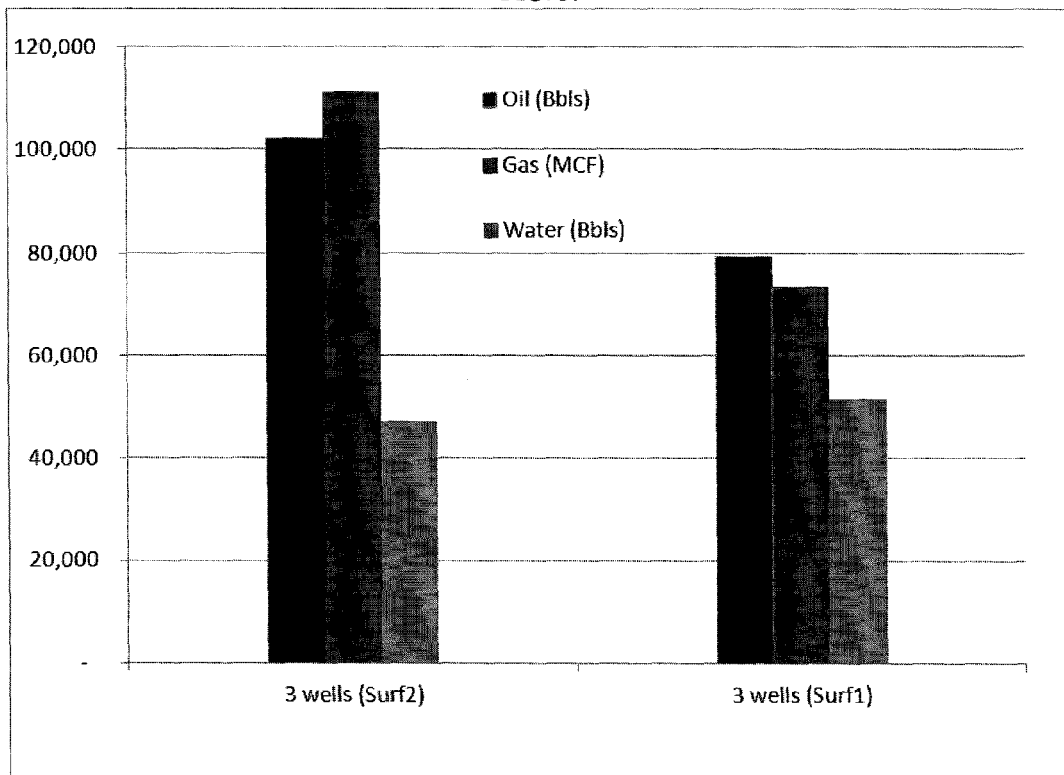
FIG. 5 is a production table illustrating the field example.

Capillary Pressure 3 grams of crushed shale core were loaded into a powder cell and connected to a force transducer. The powder cell was slowly brought to contact to a surfactant solution of 1000 ppm. The weight gain of the powder cell is recorded as a function of time. The square of weight gain is plotted against the time as illustrated by FIG. 5. The slopes of the plots are used to compare the capillary pressure. Typically, the smaller the slopes are, the lower the capillary pressure. It is evident that surf2 enables lower capillary pressure than surf1.

Example 6

Adsorption to Proppants 10 g 100 mesh proppants were added to 100 grams of 1000 ppm surfactant solutions. The solutions were shaken in a mechanical shaker and heated at the formation temperature for two hours. The surfactant solutions containing the proppants were filtered and the proppants removed. The residual surfactant amount is determined by either surface tension, titration or UV-Vis spectroscopy. Surface tension measurement is preferred. The surface tension is directly proportional to the surfactant residual. A higher surface tension corresponds to a lower residual. The surfactant with the lowest surface tension and thereby the highest residual amount was selected.

Example 7

Performance Index

The above-mentioned tests need not be performed in the same order. A performance index can be assigned to a surfactant, based on the scores from each single test, 10 being the best and 1 being the poorest, respectively. Typically, a surfactant is selected and recommended for field applications if its performance index exceeds 35. The performance indices for surf1 and surf 2 are indicated below.

| Properties | Surf1 | Surf2 |
|---|---|---|
| Water solubility | 10 | 10 |
| Dynamic surface tension | 5 | 8 |
| Interfacial surface tension | 6 | 8 |
| Emulsion tendency | 1 | 8 |
| Oil recovery | 4 | 8 |
| Capillar pressure | 5 | 7 |
| Adsorption to proppants | 4 | 6 |
| Total score | 35 | 55 |

Field Example

A surfactant (surf 2) selected from the above-mentioned test matrix was evaluated in a shale formation in South Texas. Initial results shown in FIG. 5 after the first 45 days suggest that the selected surfactant has increased the oil production by 25%, gas production by 50%, as compared to other wells using the previous surfactant.

What is claimed is:
1. A method comprising:
   sampling water in a subterranean formation;
   providing at least two surfactants;
   mixing each of the surfactants with the formation water to form surfactant/water samples;
   determining a solubility of each surfactant in the formation water;
   comparing the solubility of each surfactant with the solubility of each other surfactant;
   assigning a solubility performance value for each surfactant based, at least in part, on its solubility in the formation water sample compared to the solubility of each other surfactant;

assigning a performance index to each surfactant based, at least in part, on its solubility performance value; and determining whether each surfactant is suitable for use in the formation based, at least in part, on its performance index.

2. The method of claim 1, wherein the step of determining the solubility of each surfactant is performed with a turbidity meter and the step of comparing the solubility of each surfactant is performed by comparing a percent turbidity of the surfactant/water samples.

3. The method of claim 1 further comprising:
determining a diffusion coefficient of each surfactant/water sample;
comparing the diffusion coefficient of each surfactant/water sample; and
assigning a diffusion coefficient performance value for each surfactant based, at least in part, on the diffusion coefficient of the corresponding surfactant/water sample compared to each other surfactant, wherein the performance index for each surfactant is assigned based, at least in part, on its diffusion coefficient performance value.

4. The method of claim 3, wherein the step of determining the diffusion coefficient comprises:
measuring surface tension and surface age time data for each surfactant/water sample;
determining the characteristic time $\tau_d$ and the equilibrium surface tension $\gamma_{eq}$ by fitting the equation:

$$\Delta\gamma(t \gg \tau_d) \cong \Delta\gamma_{eq}\left(1 - \sqrt{\frac{\tau_d}{t}}\right)$$

to the surface tension and surface age time data; and
determining the diffusion coefficient from a molecular size a and a volume fraction $\phi_b$ of each surfactant according to the equation:

$$D \cong \frac{1}{\phi_b^2}\frac{a^2}{\pi\tau_d}.$$

5. The method of claim 1 further comprising:
sampling crude oil in the formation;
mixing the crude oil with the surfactants to form crude oil/surfactant samples;
mechanically agitating the crude oil/surfactant samples;
determining a phase separation rate of each crude oil/surfactant sample;
comparing the phase separation rate of each crude oil/surfactant sample; and
assigning a phase separation rate performance value for each surfactant based, at least in part, on the phase separation rate of the corresponding crude oil/surfactant sample compared to the phase separation rate of each other surfactant, wherein the performance index for each surfactant is assigned based, at least in part, on its phase separation rate performance value.

6. The method of claim 5, wherein the step of determining the phase separation rate comprises:
calculating the phase separation rate from the slope of the curve ΔTransmission or BackScattertng=$f$(Time).

7. The method of claim 1 further comprising:
supplying a crushed core plug from the formation saturated with oil from the formation;
forming a surfactant solution for each surfactant;
passing the surfactant solution for each surfactant through the crushed core plug to form an effluent;
determining an oil recovery from the effluent for each surfactant;
comparing the oil recovery for each surfactant; and
assigning an oil recovery performance value for each surfactant based, at least in part, on the oil recovery of the corresponding surfactant compared to the oil recovery of each other surfactant, wherein the performance index for each surfactant is assigned based, at least in part, on its oil recovery performance value.

8. The method of claim 7, wherein the oil recovery is determined by using infrared spectroscopy.

9. The method of claim 1 further comprising:
supplying a crushed core plug from the formation;
contacting the crushed core plug with each surfactant;
determining a capillary pressure for each surfactant;
comparing the capillary pressure for each surfactant; and
assigning a capillary pressure performance value for each surfactant based, at least in part, on the capillary pressure of the corresponding surfactant compared to the capillary pressure of each other surfactant, wherein the performance index for each surfactant is assigned based, at least in part, on its capillary pressure performance value.

10. The method of claim 9, wherein the step of determining the capillary pressure for each surfactant further comprises:
determining a weight gain of the crushed core plug;
plotting the square of the weight gain versus time; and
determining the slopes of the plots.

11. The method of claim 1 further comprising:
selecting a proppant for use in the formation;
contacting the proppant with each surfactant;
determining a surface tension for each surfactant;
comparing the surface tension for each surfactant; and
assigning a surface tension performance value for each surfactant based, at least in part, on the surface tension of the corresponding surfactant compared to the surface tension of each other surfactant, wherein the performance index for each surfactant is assigned based, at least in part, on its surface tension performance value.

12. The method of claim 11, wherein the step of determining the surface tension further comprises:
measuring a residual surfactant.

* * * * *